(12) United States Patent
Cullum et al.

(10) Patent No.: US 7,528,952 B2
(45) Date of Patent: *May 5, 2009

(54) HAND-HELD FLUORESCENCE POLARIMETER

(75) Inventors: Malford E. Cullum, Grayslake, IL (US); Istvan Naday, Naperville, IL (US); Alan L. McArthur, Mokena, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 337 days.

This patent is subject to a terminal disclaimer.

(21) Appl. No.: 11/148,572

(22) Filed: Jun. 2, 2005

(65) Prior Publication Data

US 2005/0272145 A1 Dec. 8, 2005

Related U.S. Application Data

(63) Continuation-in-part of application No. 10/700,868, filed on Nov. 5, 2003.

(51) Int. Cl.
*G01J 3/00* (2006.01)
*G01J 4/00* (2006.01)
*C12M 1/00* (2006.01)
*C12M 3/00* (2006.01)

(52) U.S. Cl. .............. 356/368; 356/300; 356/364; 435/283.1; 435/287.1; 435/287.2

(58) Field of Classification Search ............. 424/184.1, 424/1.11, 10.1; 436/500, 543, 546
See application file for complete search history.

(56) References Cited

U.S. PATENT DOCUMENTS 4,516,856 A * 5/1985 Popelka ................ 356/368
6,999,173 B2 * 2/2006 Kleinfeld et al. ........... 356/417

* cited by examiner

*Primary Examiner*—Robert Mondesi
*Assistant Examiner*—Vanessa L. Ford
(74) *Attorney, Agent, or Firm*—Joseph K. Hemby; Ning Yang

(57) ABSTRACT

A small, portable, hand-sized apparatus for detecting microorganisms or chemicals in liquid samples by fluorescence polarization. The apparatus operates using a low power excitation light source, such as an LED, in order to irradiate a sample with polarized light. Detection of emitted polarized light from the sample is detected in multiple planes simultaneously using low power detectors resulting in an elimination of error caused by drifts in intensity in sequential measurements and in reducing assay time.

6 Claims, 1 Drawing Sheet

HAND-HELD FLUORESCENCE POLARIMETER

The present application is a continuation in part of application Ser. No. 10/700,868, filed 11/05/2003. The application Ser. No. 10/700,868 is hereby incorporated by reference.

FIELD OF INVENTION

The present invention relates to a miniaturized, portable, hand-held apparatus for measuring the fluorescence polarization of a liquid sample.

BACKGROUND OF INVENTION

Fluorescence Polarization as a Detection/Diagnostic Tool

Immunization strategies to specific disease causing organisms and toxins are being developed and implemented aimed at prophylactically inhibiting disease processes. However, many important public health related organisms remain for which no prophylactic measures are available or can be practicably administered on a wide scale. In these cases prophylactic screening is required to ensure early treatment.

Currently available methods for the detection of pathogen exposure, infection and diagnosis varies depending on the target organism. Most diagnostic methods, however, require a biological sample, such as blood or serum, to be obtained and tested for the presence of antibody specific to the target organism or for antigen. The assay methods generally performed are modifications to surface-binding, heterogeneous assays such as enzyme-linked immunosorbant assay (ELISA), radioimmunoassay (RIA), or agglutination. Since these assays require the interaction of antigen with a specific surface, there is often exhibited significant high non-specific binding and concomitant loss of specificity.

Fluorescence polarization (FP) overcomes many of the inherent problems encountered with most surface-binding antibody-based assays. FP is the process in which visible or ultraviolet light is polarized with a filter and illuminates a fluorochrome attached region of a target molecule, that in turn fluoresces, emitting light of longer wavelength whose signal is captured and recorded (1). The emitted light retains its polarization in solutions containing slower turning, large molecule-fluorochrome complexes compared with the presence of smaller labeled molecules. Different fluorochromes can be chosen to accommodate molecules of different sizes up to $10^7$ kDa molecular weight (2).

FP assays have been utilized to measure different types of binding reactions to follow proteolytic reactions with and without their inhibitors and to measure various other enzymatic or receptor binding reactions (3, 4). In clinical settings, FP is used to measure the level of drugs, hormones or antibodies in blood plasma (5). Furthermore, the value of using FP diagnostic methods for the diagnosis of infection using other, non-serum matrixes, such as oral fluids and saliva, is gaining recognition (6).

Consequential to the recognized uses of FP, methods utilizing FP for detection of a number of target moieties have been developed. U.S. patent to Wang, et al. (7) discloses a method and reagents for determining a ligand, particularly steroid, hormone, anti-asthmatic, anti-neoplastic, anti-arrhythmic, anti-convulsant, antibiotic, anti-arthritic, antidepressant, cardiac glycoside, or a metabolite thereof, in biological fluids such as serum, plasma, spinal fluid, amnionic fluid, and urine. In particular, Wang, et al. relates to a specific class of tracer compounds required as reagents in such procedures. Additionally, a U.S. patent to Jolley, et al. (8) discloses a homogeneous immunoassay in which a fluorophore-conjugated lipopolysaccharide derived bacterial antigen is reacted with antibodies specific for the antigens in a diluted serum specimen, with quantitative detection of the formation of an immune complex obtained by measuring the change in fluorescence polarization after complex formation.

U.S. patent to Nakayama, et al. (9) discloses a fluorescence polarization method for analyzing a target moiety in a given sample. The procedure employs the steps of: (a) providing a fluorescent-labeled protein in which a protein is covalently bound to a fluorochrome(s), wherein the protein is capable of specifically binding to the assay-object; (b) allowing the fluorescent-labeled protein to bind to the assay-object; and (c) measuring a change in the degree of fluorescence polarization which has taken place in the fluorescent-labeled protein by its binding to the assay-object.

Knowledge of the epidemiology of diseases is important in health care planning and treatment. Both planning and treatment are dependent upon accurate and rapid diagnosis. FP technology is highly amenable to the accurate estimation of concentrations of diagnostic markers, drugs and chemicals, or bio-hazardous agents, in clinical as well as environmental samples, using a range of different fluid matrixes.

Although analysis of serum for the presence of specific hormones, drugs, antibodies and antigens routinely used, saliva and oral fluids are biochemically distinct and have been increasingly recognized as acceptable alternatives. Unlike serum samples, oral fluids are collected without pain, needle sticks, or religious and social prohibitions, and their use involves minimal risk or exempt protocols for the use of human subjects. Therefore, the use of FP using serum or oral fluids can be utilized to accurately detect or diagnosis markers, drugs, chemicals or specific biohazardous agents within a few seconds to several minutes. Additionally, FP is useful for the evaluation of environmental samples including water sources for the presence of contaminating chemicals or microorganisms. The applicability of FP assay methods to the analysis of a broad spectrum of sample sources, unlike many antibody-based or molecular-based methods, is partially due to the relative robustness of FP which is unaffected by constituents in non-homogeneous samples, such as whole blood, saliva or even environmental samples. Specificity of FP assays can be readily designed to be generally very high, with a specificity approaching or exceeding approximately 98%.

A significant limitation of current FP methods, however, are the size and power requirements of available instrumentation. These constraints are particularly acute in field settings, small clinical settings or in third world health care environments where infrastructure is limited. Therefore, there has been a long-felt need for more compact and simplified FP devices. The advent of new, compact devices will permit an expansion of effective, noninvasive as well as accurate laboratory quality diagnostic tests performed in field settings.

Prior Art Fluorescence Polarization Instrumentation

Early FP instruments required relatively high wattage and relatively intense light sources, such as 200-250 watt mercury or xenon gas discharge lamps. This was necessary in order to obtain the desired emission radiation from the sample at a signal to noise level ratio sufficient for detection and amplification by a low-noise photomultiplier tube and associated electronics (10). Such high wattage, bright lamps also required substantial cooling in order to maintain the integrity of the optical system. However, an improved fluorescence polarization instrument is disclosed in a U.S. patent to Popelka (11). The Popelka patent discloses an optical system for a fluorescent polarization instrument including a low wattage, low intensity focused light source and a polarizer/liquid crystal combination in the excitation path focusing excitation light of alternate planes of perpendicular polarization onto a fluorescent liquid sample, wherein emitted light from the fluorescent sample is filtered, polarized and focused onto a photo-multiplier for processing. Popelka, additionally discloses a series of non-reflective baffles placed around the sample to reduce reflections and a means to monitor the excitation light while maintaining a substantially constant intensity level focused on the sample, while the low wattage, low intensity light source is provided by a 50 watt tungsten halogen projector lamp.

Despite recent technological improvements in FP technology, FP instruments remain relatively large and bulky with high voltage and high power requirements and error in measurement due to drifts in intensity of fluorescence due to the relatively extended time required in conducting sequenctial FP measurements in horizontal and vertical planes.

Thus, despite the technological promise of FP as an assay method of choice in many scenarios, there has been long-felt need for instruments that are significantly reduced in size and complexity over prior art FP devices and that are capable of operation with a low power supply such as a battery pack or other low power DC power source. Although improvements have been in instrument size they still remain relatively bulky and/or suffer from error inherent in sequential fluorescence measurements.

The need for sensitive yet small FP detection devices is particularly acute in military settings, as well as in civilian field settings, where operation of large table-top instruments are not possible or practical.

SUMMARY

The present invention is an fluorescence polarization instrument that is significantly reduced in size but that is capable of sensitive detection of target moieties and data confidence by inclusion of reduced intrinsic noise abatement systems integral to the device.

An exemplary embodiment of the present invention relates to an apparatus for measuring fluorescence polarization of a liquid sample. The contemplated apparatus is a multichannel FP device, containing multiple photo-detectors, such as photomultiplier tubes. An object of the invention is a low energy requiring light emission source, such as an light emitting diode, that illuminates the sample at a specific wavelength. Emitted sample light is then directed at multiple photodetectors, that may be connected to a microcontroller containing a high efficiency switch device, such that the photodetectors detect the sample emissions simultaneously, in multiple planes, verses sequentially. The microcontroller unit may also contain software which calculates and provides rapid assay results thus preventing the need for downloading of data an performing external calculations.

DESCRIPTION OF THE PREFERRED EMBODIMENTS

Figure 1:
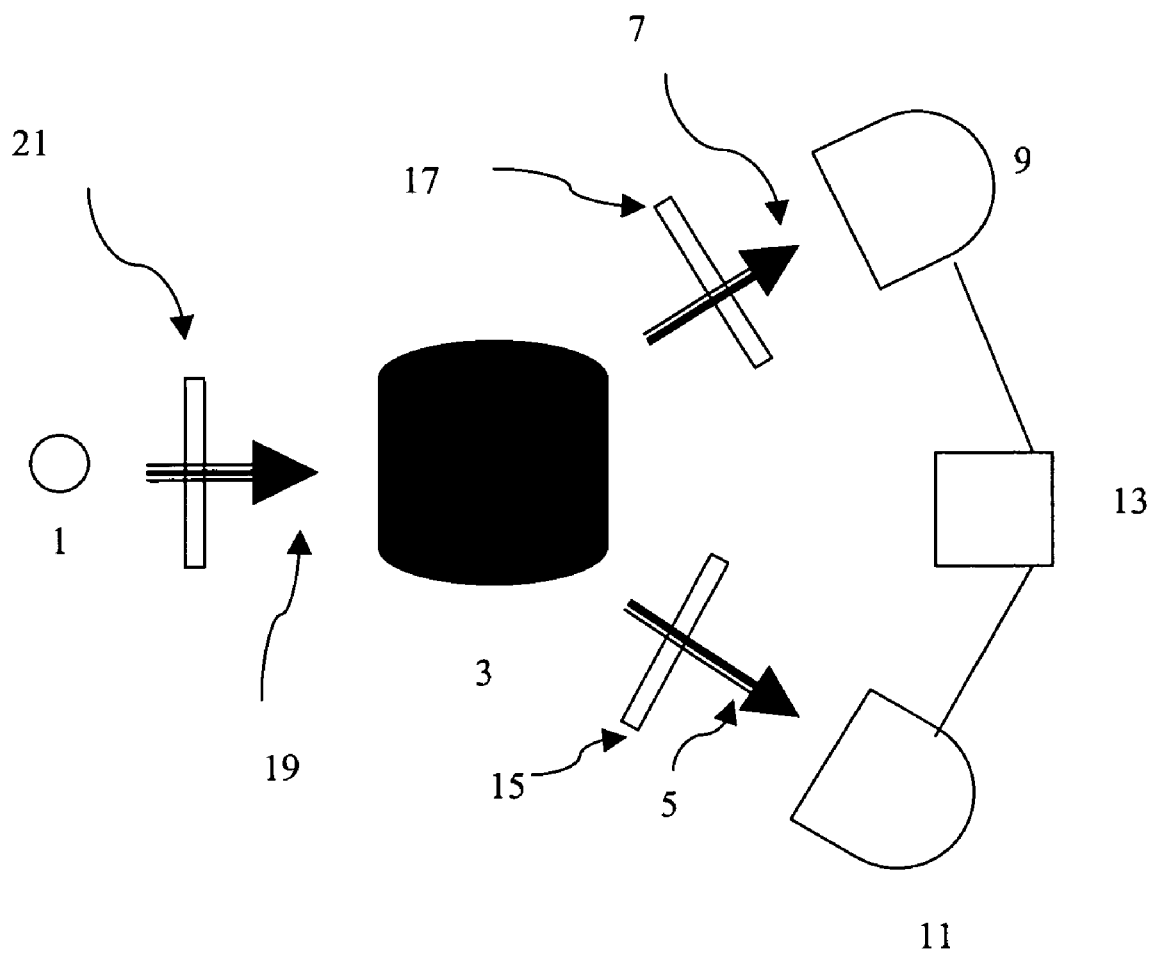
FIG. 1 is a diagram illustrating an exemplary embodiment of the inventive apparatus.

When a fluorescent liquid sample is irradiated with excitation light, the sample radiates an emission light from which the polarization, P, is determined in accordance with the expression: $I(Z)-I(Y)/I(Z)+I(Y)$, where $I(Z)$ is the measured intensity of one polarization component of the emitted light at a first polarization angle when the liquid sample is irradiated with polarized excitation light at the first polarization angle, and where $I(Y)$ is the measured intensity of the polarization component of emitted light at the first polarization angle when the liquid sample is irradiated with polarized excitation light at a second polarization angle perpendicular with respect to said first polarization angle. Using a common fluorochrome, the difference between the polarization of a reference or control sample and the polarization of a sample of interest is determined by differences in the mass of a molecule attached to the fluorochrome, as discussed in detail above.

The military, as well as other field medical activities, require the ability for rapid, field diagnostic instrumentation capable of obtaining diagnostic results similar in sensitivity and reliability as is available in clinical or hospital settings. FP devices have been utilized as the detection method of choice for a growing number of clinic and hospital based assays. The design of diagnostic devices planned solely for use in hospital settings, however, does not require the strict space and power limitations that field settings would demand. Because of the military need for hospital quality devices capable of field setting operability, small sized and low power requiring devices are needed.

The present invention relates to a small, low-power, handheld apparatus for measuring the fluorescence polarization of a liquid sample by direct or indirect assay methods. In FP direct assay, the change in rotation of the target molecule is directly measured before and following binding to another molecule, such as an antibody. Small molecules tend to rotate rapidly in solution while larger entities rotate much more slowly. Therefore, irradiation of fluorescently-labeled small molecules with polarized light will exhibit a much more rapid change polarization in emission than after the same molecule is bound by a relatively large molecule such as antibody. In an indirect assay, the rate of change in fluorescence polarization of a fluorescently-labeled molecule, that is similar to the target molecule, is monitored.

The present invention is able to combine the low power requirement of light sources such as light emitting diodes with the ability to detect sample emission, simultaneously, in multiple planes using photomultiplier tubes, avalanche photodiodes or silicone photodiodes via a highly efficient switching power supply. An exemplary embodiment is depicted in FIG. 1. In FIG. 1, polarized light 19, produced by passing light from a low energy light source 1 through polarization filers 21, illuminates a sample 3. Emitted sample light is again polarized by passing through horizontal and vertical plane filters 15 and 17. The horizontal and vertically polarized light 5 and 7 is then detected by horizontal and vertical plane 11 and 9. The photodetectors are able to simultaneously detect the light powered by the microcontroller 13. The simultaneous detection of light may be detected by any means including by photomultiplier tubes, silicone photodiodes or avalanche diodes. The simultaneous measurement configuration eliminates error caused by drifts of intensity in sequential measurement systems and reduces the affect of slow changes in behavior of the sample during the measurement cycle. Ultimately, the configuration leads to increased speed of assay operation over sequential measurement in different planes as well an increase in the accuracy of diagnostic results. The low power requiring light source and low power light detection components can then be combined with a low power microcontroller permitting a large reduction in size of the device, over the prior art, and concomitant reduction in power needs. Depending on the light source and detection components used, along with the microcontroller unit, the size of the device can be from 300 to 900 cm$^3$, at 400 to 800 g in weight with a power requirement of 1 to 2 W.

Any configuration of light paths to form a "T", "Y" "I" or "V" with respect to the illuminating source can be utilized. Alternatively, a single arm light path with an oscillating polarizer positioned after the sample compartment forming an "L" or "I" with respect to the illuminating source can be used. Furthermore, suppression of noise and signal uncertainty from horizontal and vertical emissions of the photo-multiplier is accomplished by the output signal being fed, via an ultra-low noise transimpedance amplifier, into a digital filter algorithm implemented into onboard microcontroller software.

An aspect of the invention is the ability of the FP device to conduct onboard calculations where prior art devices required down loading of tabulated data. Onboard calculation of data permits the real-time categorical assignment of results and further increases the speed of assay and final diagnosis determination. The device is capable of calculating FP values in mP units by direct FP assay, where the change in rate of rotation is directly measured on the target molecule as well as by indirect polarization assay methods where the rate of change of an equivalent fluorescently-labeled ligand molecule is measured. In either method, the device automatically determines the polarization units, in mP, converts the value into whole numbers, incorporating the background FP values into the final result determination.

For an indirect competitive immunoassay, the background FP intensity of an assay buffer in the vertical and horizontal plane is first determined, wherein $I_{Vbg}$ is the fluorescence in the vertical plane and $I_{Hbg}$ is the fluorescence in horizontal plane. This information is then stored in a respective register in the onboard microcontroller. A baseline fluorescence of the test sample pack, consisting of the test sample containing antibody specific to the target molecule, is then determined in the vertical ($I_{Vbl}$) and horizontal plane ($I_{Hbl}$). These measurements are also stored in the onboard microcontroller.

The fluorescence of the test sample pack plus tracer molecule is calculated and stored onboard, wherein the tracer is a fluorescently-labeled equivalent molecule of the target molecule, in the vertical ($I_{Vf}$) and horizontal ($I_{Hf}$) planes. The FP baseline corrected values (mP$_{blc}$) are then determined according to the formula mP$_{blc}$×1000={[($I_{Vbl}$-$I_{Vbg}$)-($I_{Hbl}$-$I_{Hbg}$)]/[($I_{Vbl}$-$I_{Vbg}$)+($I_{Hbl}$-$I_{Hbg}$)]} wherein mP$_{blc}$ is the calculated baseline in millipolarization units as a whole number, and $I_{Vbl}$ and $I_{Hbl}$ is said fluorescence of test sample pack in vertical and horizontal plane, respectively, and $I_{Vbg}$ is the background fluorescence in the vertical plane and $I_{Hbg}$ is the background fluorescence in horizontal plane. The final FP value (mP$_{fc}$) of the test sample pack plus tracer is calculated using the formula mP$_{fc}$×1000={[(($I_{Vf}$-($I_{Vbl}$-$I_{Vbg}$))-($I_{Hf}$-($I_{Hbl}$-$I_{Hbg}$))]/[(($I_{Vf}$-($I_{Vbl}$-$I_{Vbg}$))+($I_{Hf}$-($I_{Hbl}$-$I_{Hbg}$))]} wherein mP$_{fc}$ is the calculated background and baseline corrected FP value of the test sample pack in a whole number in millipolarization units, and $I_{Vfc}$ and $I_{Hfc}$ are the measurements of the test sample pack plus tracer in the vertical and horizontal planes, respectively. The calculated change (Δ) in background and baseline corrected fluorescence intensity is made, wherein mP$_A$ is the change in background fluorescence intensity in a whole number, by subtracting said mP$_{fc}$ from the mP$_{blc}$ value according to the formula mP$_A$×1000={[($I_{VA}$)-($I_{HA}$)]/[($I_{VA}$)+($I_{HA}$)]} wherein $I_{VA}$ and $I_{HA}$ are the background and baseline corrected change in fluorescence intensity determined in the vertical and horizontal planes, respectively.

The light path corrected mP value by adjusting mP$_A$ according to the formula mP$_{Alpc}$×1000={[($I_{VA}$)-($I_{HA}$)k]/[($I_{VA}$)+($I_{HA}$)k]}/G, wherein mP$_{Alpc}$ is said light path corrected mP value as a whole number, $I_{VA}$ and $I_{HA}$ are said change in fluorescence intensity determined in the vertical and horizonatal planes, respectively, k is a constants to equalize the photomultiplier tubes predetermined at a constant photocathode voltage and G is a selected constant used to normalize low and high polarization standards to the correct values for the standard substances For direct calculation of FP in mP units, background (fluorescence intensity is determined in horizontal and vertical planes as in the indirect FP assay. After determination of background fluorescence intensity, the fluorescence of the tracer molecule (t) is measured in horizontal ($I_{Ht}$) and vertical ($I_{Vt}$) planes, wherein said tracer is a small fluorescently-labeled target epitope of a specific anti-target monoclonal or polyclonal antibody. This measurement is then stored.

The FP tracer corrected values (mP$_{tc}$) of said test sample pack plus tracer is then determined according to the formula mP$_{tc}$×1000={[($I_{Vt}$-$I_{Vbg}$)-($I_{Ht}$-$I_{Hbg}$)]/[($I_{Vt}$-$I_{Vbg}$)+($I_{Ht}$-$I_{Hbg}$)]} wherein mP$_t$ is the calculated baseline in millipolarization units as a whole number, and $I_{Vt}$ and $I_{Ht}$ is said fluorescence of tracer in vertical and horizontal plane, respectively, and $I_{Vbg}$ is the background fluorescence in the vertical plane and $I_{Hbg}$ is the background fluorescence in horizontal plane. The final calculated FP value (mP$_{fc}$) of said tracer plus the biological fluid (bf) of interest is then made according to the formula mP$_{fc}$×1000={[(($I_{Vbf}$-($I_{Vt}$-$I_{Vbg}$))-($I_{Hbfs}$-($I_{Ht}$-$I_{Hbg}$))]/[(($I_{Vbf}$-($I_{Vt}$-$I_{Vbg}$))+($I_{Hbf}$-($I_{Ht}$-$I_{Hbg}$))]} wherein mP$_{fc}$ is said calculated tracer and background corrected FP value of said test sample pack in a whole number in millipolarization units, and $I_{Vfc}$ and $I_{Hfc}$ are the measurements of the biological sample plus tracer in the vertical and horizontal planes, respectively. The calculated change (A) in background and baseline corrected fluorescence intensity is calculated wherein mP$_A$ is said change in background fluorescence intensity in a whole number by subtracting said mP$_{fc}$ from said mP$_t$ value according to the formula mP$_{66}$×1000={[($I_{VA}$)-($I_{HA}$)]/[($I_{VA}$)+($I_{HA}$)]} wherein $I_{VA}$ and $I_{HA}$ are the tracer and background corrected change in fluorescence intensity determined in the vertical and horizontal planes, respectively. The light path corrected mP value is finally determined by adjusting mP$_A$ according to the formula mP$_{Alpc}$×1000={[($I_{VA}$)-($I_{HA}$)k]/[($I_{VA}$)+($I_{HA}$)k]}/G, wherein mP$_{Alpc}$ is said light path corrected mP value as a whole number, $I_{VA}$ and $I_{HA}$ are said change in fluorescence intensity determined in the vertical and horizonatal planes, respectively, k is a constants to equalize the photomultiplier tubes predetermined at a constant photocathode voltage and G is a selected constant used to normalize low and high polarization standards to the correct values for the standard substances.

Example of Handheld Fluorescence Polarimeter

A portable, lightweight, handheld FP detection apparatus is described. The apparatus is suitable and useful of detecting specific marker antibody or antigen in bodily fluids such as serum, saliva, gingival crevicular fluids, oral fluids or other environmental matrixes such as food or soil. The apparatus capable of providing quantitative detection results within 5 minutes or less.

The apparatus is approximately 15 cm long (5.9 in)×5 cm (1.97 in) deep×10 cm (3.94 in) wide and weighs approximately 500 grams. The apparatus operates on very low power, requiring only four (4) AA alkaline batteries. Furthermore, the apparatus' small size, coupled with the low power requirement, permits ready portability and the capability of conducting operations by a single operator, in the field. The apparatus is auto-calibrating with auto-on during sample insertion. The dynamic range of the apparatus is 10 pM to 10 nM with a 1 mP standard deviation at 1 nM fluorescein.

The battery and power supply of the apparatus supplies power to an ultra-low power microcontroller unit containing an ADC converter capable of sampling the amplified photomultiplier signals at a rate of approximately 1,000 times per second. The micro-controller controls all aspects of the instrument including the operator interface, opto-mechanical control, digital filtering, arithmetic computation and data storage and retrieval. Data from the operator input and test measurements is stored in a flash memory chip onboard the micro-converter. Data retrieval is accomplished via a serial port.

The apparatus, containing one excitation sub-system and two emission sub-systems was modeled using to optimize efficiency and minimize stray light. Based on these analyses, the Tee layout was preferred because of the high throughput and low stray light. The expected signal is approximately 1,200 photoelectrons/second for unpolarized samples.

Excitation and emission subsystems were optimized and evaluated lens design software. The excitation channel contains a high intensity blue light emitting diode (LED) centered at 490 nm with a bandwidth (half-height) of 10 nm. The emission channels are 530 nm with a bandwidth (half-height) of 10 nm. Silicone photodiode or avalanche diodes can be utilized as detectors. Through software optimization of the excitation and emission subsystems, the sample tube is illuminated with a collimated light beam and an emission subsystem that images the sample onto the photo-detectors. The excitation and emission subsystem arrangement eliminates error caused by intensity drifts and reduces the affect of slow changes in sample behavior. The microcontroller also contains a digital filter algorithm integral to the microcontroller software that serves to suppress the noise and uncertainty of the measured vertical and horizontal emission signals. Signal output from the photo-multiplier tube is fed into ultra-low transimpedance amplifier. The ensuing analog signal from the amplifier is then fed into the ADC input of the microcontroller.

An LED display on the face of the device indicates assay operation status, such when the assay is in progress or when completed. Additionally, a "RESULT" light will illuminate green to indicate if the sample result is available and is predicated on a large polarization unit value (P) value and thus the result is safe. If the "RESULT" light is yellow, the value is predicated on an intermediate polarization unit value thus the result is reported as marginally accurate. A red light indicates that the result is not safe due to a low polarization value. The results of 500 or more tests can be stored until the data is downloaded. The apparatus can also be programmed to enter sleep mode or to automatically shutoff after selected periods of time.

REFERENCES

1. Dandliker W., G. Feigen. 1961. Quantification of the antigen-antibody reaction by plarization of fluorescence. Biochem Biophys Res Comm. 5(4): 299-304.
2. Terpetschnig, E. H. Szmacinski, J. Lakowicz. 1995. Fluorescence polarization immunoassay of a high-molecular weight antigen based on a long-lifetime Ru-ligand complex, Anal. Biochem 227: 140-147.
3. Nasir, M, M. Jolley. 1999. Fluorescence polarization: An analytical tool for immunoassay and drug discovery, Comb Chem High Throughput Screen, 2: 177-190.
4. Nielsen, K., D. Gall, M. Jolley, et al. 1996. A homogeneous fluorescence polarization assay for detection of antibody to *Brucella abortus,* J. Immunol. Methods 195: 161-168.
5. Jolley, M. 1981. Fluorescence polarization immunoassay for the determination of therapeutic drug levels in human plasma, J. Anal Toxicology, 5: 236-240.
6. Cullum, M. E. et al. 2003. Diagnosis of militarily relevant diseases using oral fluid and saliva antibodies: Fluorescence polarization immunoassay. Mil. Med. 168(11): 915-921.
7. Wang, et al, U.S. Pat. No. 4,585,862 issued Apr. 29, 1986.
8. Jolley, et al, U.S. Pat. No. 5,976,820 issued Nov. 2, 1999.
9. Nakayama, et al., U.S. Pat. No. 6,432,632 issued Aug. 13, 2002.
10. Spencer, R. D., F. D. Toledo, B. T. Williams, and N. L. Yoss. 1973. Design, construction, and two applications for an Automated flow-cell polarization fluorometer with digital read out. Clin. Chem. 19(8): 838-844.
11. Popelka, S. R., U.S. Pat. No. 4,516,856 issued May 14, 1985.

What is claimed is:

1. An apparatus for measuring the fluorescence polarization of a liquid sample, said apparatus comprising:
   (a) a sample compartment containing said liquid sample containing one or more analytes;
   (b) a low power light emitting diode as an excitation light sources for irradiating said sample compartment with excitation light;
   (c) two or more emission detectors operatively connected to said light emitting diode to simultaneously detect the polarized emission light from said sample compartment in at least two planes.

2. The apparatus of claim 1, wherein said emission detectors are selected from the group consisting of photomultiplier tubes, silicone photodiode and avalanche photodiodes.

3. The apparatus of claim 1, wherein said apparatus is 400 to 800 g in weight.

4. The apparatus of claim 3, wherein said apparatus has a size of 300 to 900 cubic centimeters.

5. The apparatus of claim 4, wherein said apparatus can be operated on 1 to 2 watts of power.

6. The apparatus of claim 1, 3, 4 or 5 further comprising a microcontroller operable to calculates-and save fluorescence polarization as mP units.

\* \* \* \* \*